(12) United States Patent
Kommareddy et al.

(10) Patent No.: US 8,058,621 B2
(45) Date of Patent: Nov. 15, 2011

(54) ELEMENTAL COMPOSITION DETECTION SYSTEM AND METHOD

(75) Inventors: Vamshi Krishna Reddy Kommareddy, Bangalore (IN); Paul Joseph Martin, Ballston Spa, NY (US); Saratchandra Shanmukh, Bangalore (IN); Paul Burchell Glaser, Albany, NY (US); Susanne Madeline Lee, Cohoes, NY (US); Ramakrishna Rao, Bangalore (IN); Manoharan Venugopal, Bangalore (IN)

(73) Assignee: General Electric Company, Niskayuna, NY (US)

( * ) Notice: Subject to any disclaimer, the term of this patent is extended or adjusted under 35 U.S.C. 154(b) by 79 days.

(21) Appl. No.: 12/605,391

(22) Filed: Oct. 26, 2009

(65) Prior Publication Data
US 2011/0095190 A1   Apr. 28, 2011

(51) Int. Cl.
*G01N 33/22* (2006.01)
(52) U.S. Cl. ...................................... 250/364
(58) Field of Classification Search ........... 250/364; 378/45
See application file for complete search history.

(56) References Cited

U.S. PATENT DOCUMENTS

| | | | |
|---|---|---|---|
| 5,430,786 A * | 7/1995 | Komatsu et al. | 378/45 |
| 5,517,427 A | 5/1996 | Joyce | |
| 6,121,628 A | 9/2000 | Rising | |
| 6,122,344 A * | 9/2000 | Beevor | 378/88 |
| 6,272,203 B1 * | 8/2001 | Yoneda et al. | 378/45 |
| 6,644,095 B2 | 11/2003 | Van Mullekom et al. | |
| 6,810,718 B2 | 11/2004 | Wilson et al. | |
| 7,258,098 B2 | 8/2007 | Kim | |
| 7,738,630 B2 * | 6/2010 | Burdett et al. | 378/85 |
| 2004/0131146 A1 * | 7/2004 | Chen et al. | 378/41 |
| 2005/0086275 A1 * | 4/2005 | Moore et al. | 708/200 |
| 2008/0075229 A1 * | 3/2008 | Ryan | 378/70 |
| 2008/0159474 A1 * | 7/2008 | Hubbard-Nelson et al. | 378/45 |
| 2010/0200104 A1 * | 8/2010 | Fleischer et al. | 141/1 |

FOREIGN PATENT DOCUMENTS

EP   1967568 A1 *  9/2008

* cited by examiner

*Primary Examiner* — David Porta
*Assistant Examiner* — Marcus Taningco
(74) *Attorney, Agent, or Firm* — Ann M. Agosti

(57) ABSTRACT

A system to detect a plurality of elements is proposed. The system includes one or more X-ray sources for transmitting X-rays towards a sample and also includes plurality of photon detectors. An array of crystals are arranged in a curvature with appropriate geometry for receiving a plurality of photon energies emitted from the sample and focusing the photon energy on the plurality of detectors. The plurality of photon detectors are spatially arranged at Bragg angles corresponding to signature photon energies to detect the plurality of elements simultaneously.

21 Claims, 5 Drawing Sheets

ELEMENTAL COMPOSITION DETECTION SYSTEM AND METHOD

BACKGROUND

The subject matter disclosed herein generally relates to detection of contaminants in fuel and in particular to monitoring and conditioning of gas turbine fuel.

Fuel composition, among other things, influences the corrosion and hence the life of component material in a gas turbine. Fuel may include hydro-carbon based gases and liquids that are directly combusted to produce energy. Elements in the periodic table such as sulfur, sodium, vanadium, potassium, calcium, lead, etc. that may be present as contaminants in the fuel cause degradation of alloy coatings. For example, oxides of sulfur and vanadium may react with other contaminants to form sulfates and vanadates that are corrosive at high temperatures. Typically, the presence of contaminants in fuel, such as sodium, potassium, and vanadium result in deposits from the combustion process that damage the protective surface coating of gas turbine components.

Gas turbine life is affected by corrosion of different components. Fuel composition is a significant contributor to corrosion in gas turbines. The concentration levels of elemental contaminants in the fuel influence gas turbine performance and maintenance in general. Furthermore, contaminants influence degradation of parts of the gas turbine that are exposed to hot-gas including combustors, transition pieces and turbine buckets. Contaminants contained in compressor inlet air, injected steam, and water may also contribute significantly to corrosion. Conventional methods to check for fuel contaminants include manual sampling and testing using a rotating disc emission (RDE) spectrometer. Such methods are prone to corruption of the fuel sample that may arise due to mishandling or poor sampling techniques. Frequent sampling is required at locations where fuels are susceptible to having high contaminant levels. Such frequent sampling is time consuming and labor intensive.

It is desirable to have an online fuel analysis system that provides an ability to track elemental contaminant concentrations in real time. Further, such real time monitoring of fuel would enable timely corrective action and reduce instances of unscheduled maintenance.

BRIEF DESCRIPTION

Briefly, a system to detect a plurality of elements is proposed. The system includes one or more X-ray sources for transmitting X-rays towards a sample and also includes plurality of photon detectors. An array of crystals are arranged in a curvature with appropriate geometry for receiving a plurality of photon energies emitted from the sample and focusing the photon energy on the plurality of detectors. The plurality of photon detectors are spatially arranged at Bragg angles corresponding to signature photon energies to detect the plurality of elements simultaneously.

In one embodiment, an online fuel monitoring system for a gas turbine system is proposed. The system includes a fuel sampling unit coupled to a fuel supply line of the gas turbine to sample a fuel in real time. The system further includes an element detection system having one or more X-ray sources for transmitting X-rays towards a sample, one or more photon detectors, and one or more crystals arranged in a curvature with appropriate geometry for receiving one or more photon energies emitted from the sample. The crystals are further configured for focusing the one or more photon energies on the one or more detectors, wherein the one or more photon detectors are spatially arranged at Bragg angles corresponding to signature photon energies to detect one or more elements. The system further includes a processor coupled to the element detection system and configured to compute a concentration of the one or more elements in the fuel sample.

In another embodiment, a system to detect vanadium in a gas turbine fuel is presented. The system includes one or more X-ray sources to generate and transmit X-rays towards a gas turbine fuel sample. The system further includes one or more X-ray optic crystals aligned to receive one or more photon energies emitted by the sample and to reflect photons having an energy level of about 4.95 kilo electron volts. The system includes a photon detector disposed at a predetermined location in a reflected path of the X-ray optic crystal and configured to detect photons having an energy of about 4.95 kilo electron volts.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Typical operating parameters that are monitored during the functioning of a gas turbine include starting cycle, power output, fuel flow, and injection rate of steam/water. Various fuels, including but not limited to natural gas, crude oils and residual fuels, are used for combustion in gas turbines. Fuel composition influences corrosion and hence the life of various components within the gas turbine such as turbine buckets and hot-gas path components. The use of fuels comprising contaminants such as sulfur, sodium, potassium, and vanadium are known to cause degradation of alloy coatings and substrate alloys of the turbine components. These contaminants may be inherent in the fuel or may have been added during poor handling/processing techniques. Molten eutectic salt mixtures of sulfates and vanadates formed at high temperatures in the gas turbine dissolve the protective oxide coating on the surface of the blades and influence the life of hot-gas-path components in the gas turbine. Certain embodiments of the invention include detection and online monitoring of contaminants and concentration of elements in the fuel.

Figure 1:
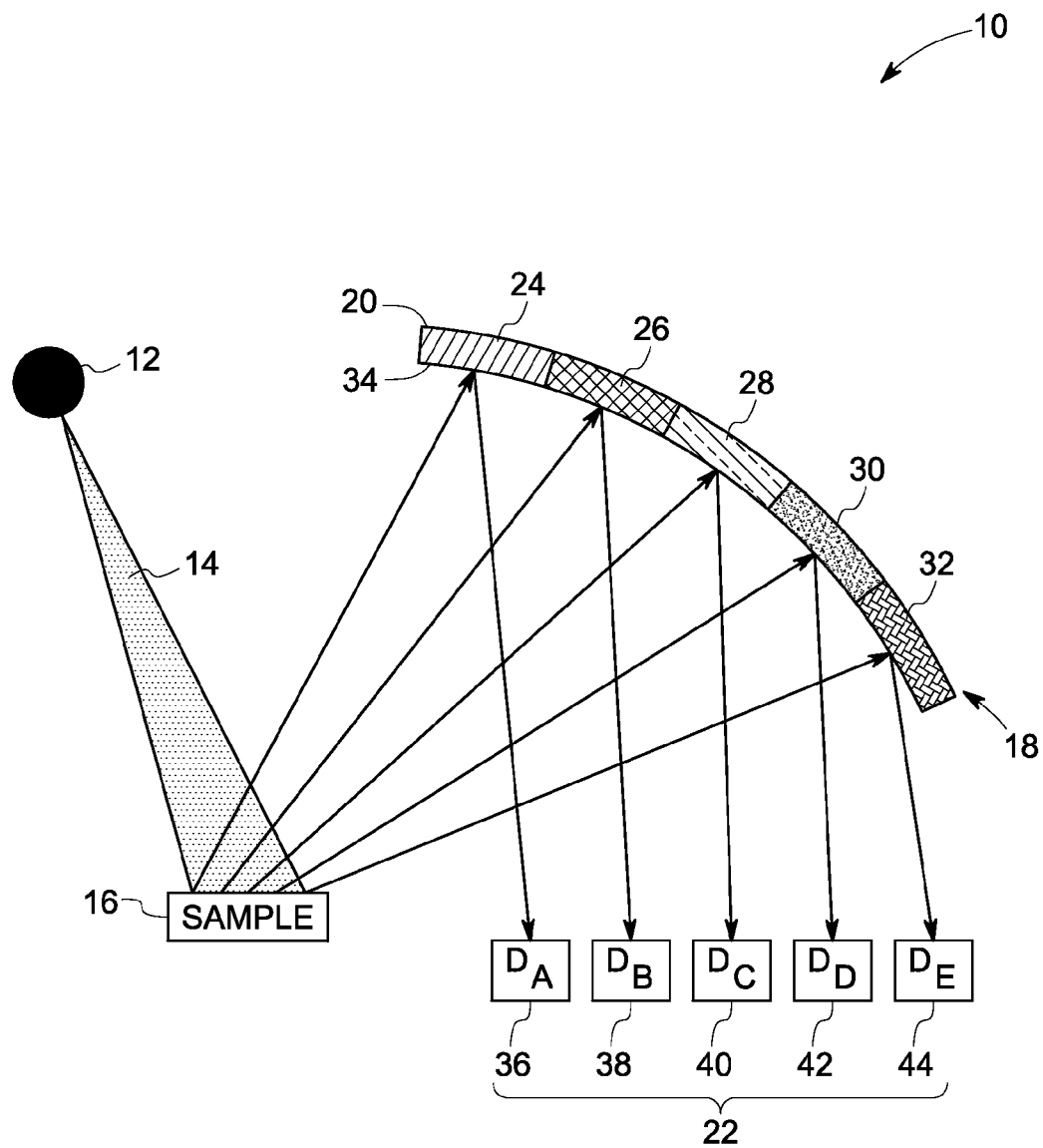
FIG. 1 illustrates an elemental detection system according to an embodiment of the invention.

FIG. 1 illustrates an elemental detection system according to an embodiment of the invention. The system 10 includes one or more X-Ray sources 12 for transmitting X-Rays 14. The X-Ray sources 12 may generate polychromatic and monochromatic radiation, and may include a single anode target. Other contemplated configurations of X-Ray source 12 include multiple anode targets with filters and/or X-ray optics, such as multi-layers or crystals. In an exemplary embodiment the X-Ray source is configured for generating a plurality of monochromatic photon beams, an X-Ray source with multiple anode targets generating multiple polychromatic photon beams, an X-Ray source with an anode target that is an alloy of multiple elements, multiple X-Ray sources, synchrotron sources and one or more X-Ray lasers. In an exemplary embodiment, the X-Ray source 12 is configured to generate X-Rays of a high flux to quantify constituent elements. The high flux source may be equipped with a rotating anode target, c-flex anode, or stationary anode coupled to a focusing X-ray optic, wherein the X-ray optic may include one of a poly-capillary, total internal reflection multilayer, or three dimensional curved crystal optic.

The X-Rays 14 from the X-Ray sources 12 are directed towards a sample 16 that includes, for example, a gas turbine fuel. Arrays of crystals 18 are arranged in a curvature 20 with appropriate geometry for receiving and focusing multiple photon energy (or fluorescence) on a plurality of photon detectors 22. In one embodiment, the array of crystals 18 includes multiple crystals such as 24-32. Each such crystal 24, 26, 28, 30, 32 may be singly curved within its inner surface 34 or doubly curved or multi-layered. The geometry of the curvature 20 may include but is not limited to toroidal, ellipsoidal, and paraboloidal surfaces or combination of these surfaces. The photon detectors 22 are spatially arranged at Bragg angles corresponding to signature photon energies. In one embodiment, each photon detector is disposed at a predetermined location to detect an element. For example, a photon detector to detect vanadium is disposed at a predetermined location, wherein the location is calculated according to the energy and Bragg angle of the transmitted photons characteristic of vanadium. Each photon detector 36, 38, 40, 42, 44 may include but not limited to one or more of a solid-state detector, a silicon drift detector, a gas proportional flow counter, a scintillation counter, and a charge coupled detector. In another exemplary embodiment, the photon detector may include a pixilated silicon detector that is sensitive to energy levels of photons.

In an exemplary operation, the element detection system 10 is configured to detect multiple elements simultaneously in the sample 16. The X-Ray source is configured to direct an X-Ray beam towards the sample 16. As discussed above, the X-Rays may include a high flux polychromatic beam or one or more monochromatic beams emitted from one or more monochromatic X-Ray sources. Multiple photon energies are emitted by the sample, upon incidence of such X-Rays. Each such photon energy is associated with a corresponding element in the sample, referenced as a signature photon energy for the element. For example, an energy level of about 4.95 kilo electron volts corresponds to vanadium. Multiple signature photon energies are detected simultaneously to detect multiple elements. Other non-limiting examples of elements to be detected include magnesium, sodium, lithium, potassium, calcium, sulfur, nickel and lead.

Figure 2:
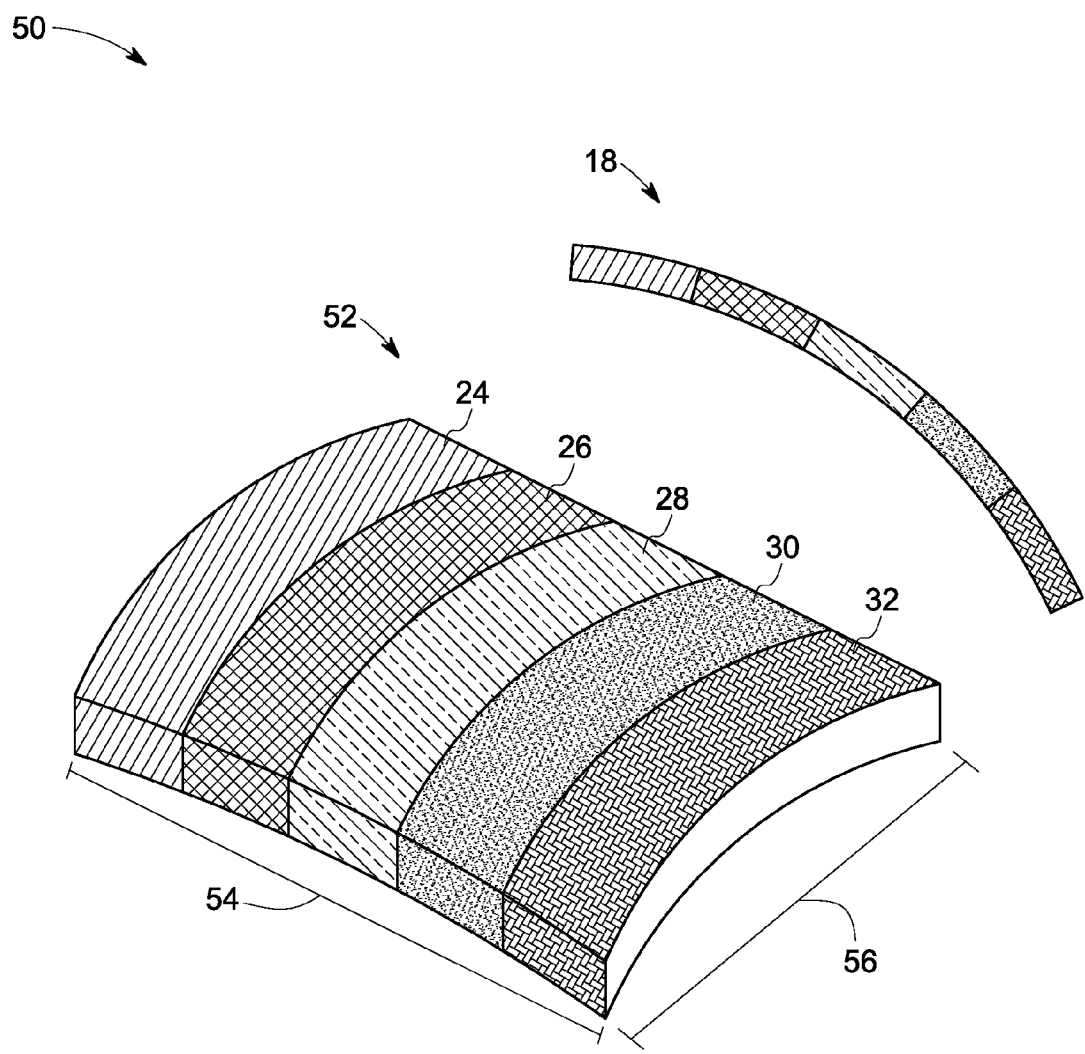
FIG. 2 illustrates a perspective view of the array of crystals in FIG. 1.

FIG. 2 illustrates a perspective view of the array of crystals in FIG. 1. An array of crystals 18 as illustrated by the reference numeral 50 is configured for receiving multiple photon energies emitted from the sample 16 and to focus each such photon energy onto a corresponding photon detector 22 as referenced in FIG. 1. Reference numeral 52 illustrates a perspective view of the array of crystals 18 wherein multiple crystals 24-32 are stacked beside each other on a curved surface. Each crystal 24, 26, 28, 30, 32 includes a curved lattice along the width 54 and along the length 56. Such multiple crystals 24-32 help capture a large solid angle of fluorescent photons from the sample and diffract or reflect multiple photons having multiple energies (or wavelengths). For example, crystal 24 is configured to diffract or reflect a particular wavelength $\lambda_1$ emitting from the sample. Further, crystals 26, 28, 30, 32 are configured to diffract or reflect corresponding wavelengths $\lambda_2, \lambda_3, \lambda_4, \lambda_5$. The curvatures along the width 54 and length 56 help focus the diffracted or reflected photon energies with higher intensity.

Figure 3:
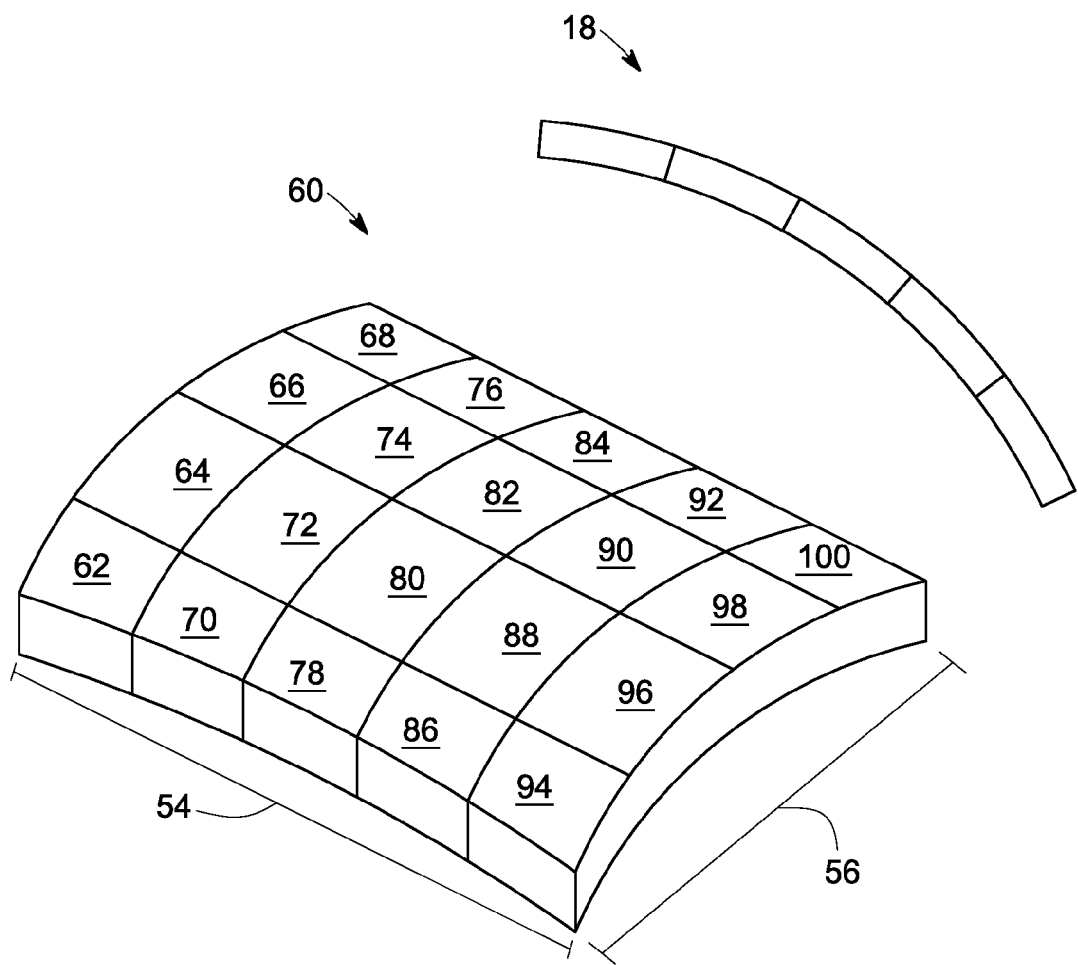
FIG. 3 illustrates an alternate configuration of the array of crystals in FIG. 1.

FIG. 3 illustrates an alternate configuration of the array of crystals in FIG. 1. The array of crystals as illustrated in the perspective view by the reference numeral 60 includes multiple crystals along the width 56. For example, multiple crystals 62-68 are arranged along the width of the array 56. Similarly, multiple such sets of crystals, 70-76, 78-84, 86-92, 94-100 are arranged closely to form a plane or a curved surface along the width 56 and length 54. One of the crystal sets, for example, 62-68 may be configured to diffract or reflect a particular wavelength $\lambda_1$. Accordingly, the remaining crystal sets 70-76, 78-84, 86-92, 94-100 may be configured to diffract or reflect respectively wavelengths $\lambda_2, \lambda_3, \lambda_4, \lambda_5$. Alternatively, the crystal sets may be arranged along rows to diffract or reflect a particular wavelength. For example, 62, 70, 78, 86, 94 may be configured to diffract or reflect a particular wavelength $\lambda_1$. In such a configuration, crystal sets along the length 54 are configured to diffract or reflect a particular wavelength.

Figure 4:
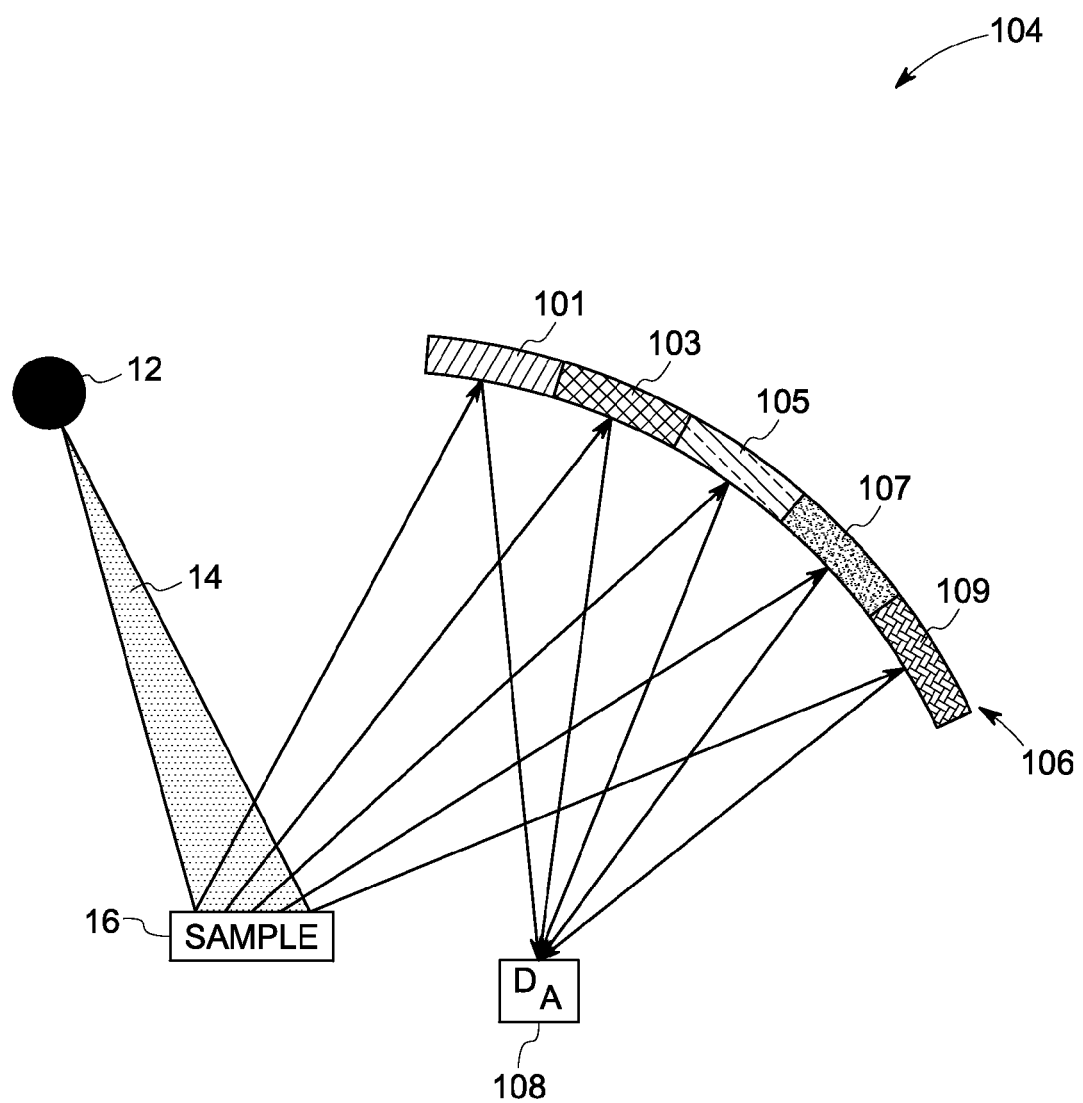
FIG. 4 illustrates an elemental detection system according to another embodiment of the invention.

FIG. 4 illustrates an elemental detection system according to an embodiment of the invention. In an exemplary embodiment, the system 104 is configured to detect a very low concentration level of vanadium in a fuel sample. The system 104 includes one or more X-Ray sources 12 configured to generate and transmit X-Rays 14 towards a sample 16. An X-Ray optic crystal 106 is aligned to receive photon energies emitted by the sample and to diffract or reflect photons having an energy level of about 4.95 kilo electron volts towards a photon detector 108. The optic crystal 106 may include multiple crystals 101-109 and arranged in a curvature. In one embodiment, the crystals 101-109 include a singly curved crystal, doubly curved crystal, multilayered crystal or combinations thereof. Photon detector 108 is disposed at a predetermined location in a reflected path of the X-Ray optic crystal and configured to detect photons having energy of about 4.95 keV, which corresponds to a wavelength of about 0.25 nanometers. The X-Ray optic crystal 106 may include one of the configurations as discussed in FIGS. 2 and 3. In one embodiment, all the crystals in the array 106 are configured to reflect a particular wavelength such that higher intensities of fluorescent photon energies are incident on the detectors. In turn by detecting such higher photon intensities, lower concentration levels of elements, for example to a lower detection limit of about 0.1 ppb (parts per billion) may be detected. In an exemplary embodiment, the elemental detection system 104 may be part of an online monitoring system.

Figure 5:
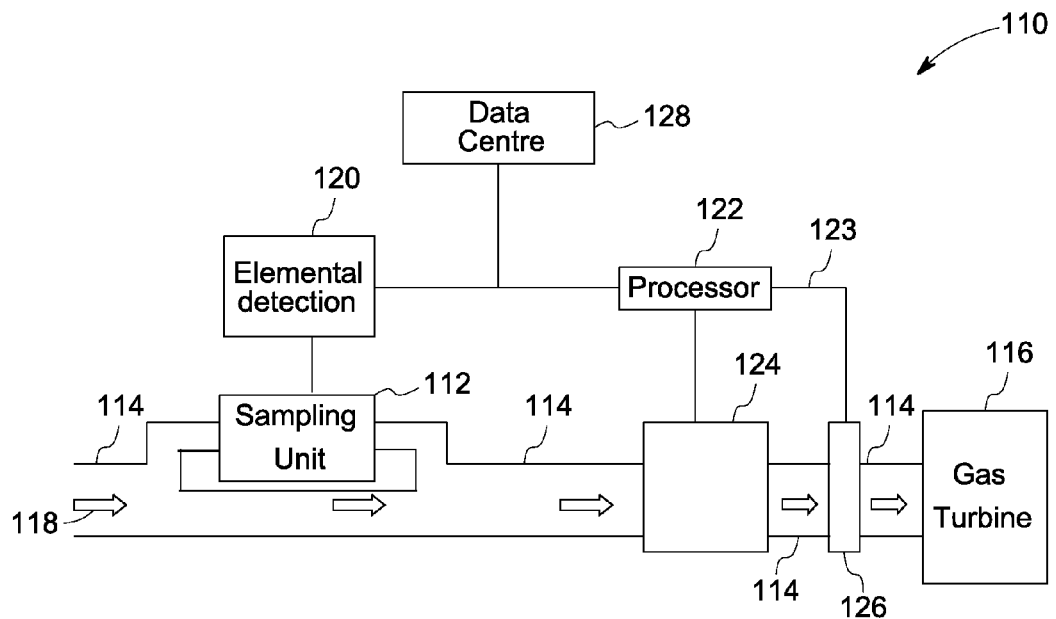
FIG. 5 illustrates an online gas turbine fuel monitoring system according to an embodiment of the invention.

FIG. 5 illustrates an online fuel monitoring system of a gas turbine according to an embodiment of the invention. The online system 110 includes a fuel sampling unit 112 coupled to a fuel supply line 114 of a gas turbine 116 to sample a fuel 118 in real time. As used herein, the term "real time" refers to a measurement condition that is exact or close to being time coherent with the current status of the parameter being measured. "Online" refers to a system that is physically attached to the system being monitored, and is continuously providing information relative to system condition without manual intervention. It may be noted that the reference to a gas turbine herein is exemplary. Such online monitoring systems may be implemented in any power generation platform requiring solid, liquid or gaseous fuel including but not limited to a gas turbine power generation platform, steam turbines, steam generating plants, boilers, or combined cycle power plants. An elemental detection system 120 is coupled to the sampling unit 112. In one embodiment, the elemental detection system 120 includes a system configuration as described in FIG. 1. A processor 122 is coupled to the elemental detection system 120 and configured to compute a fuel quality signal 123. The processor as referenced here may include any digital/analog circuitry for acquiring, computing, or analyzing system data for information storage, or for determining command signals for control actions to improve system condition and performance. A fuel delivery system 124 is coupled to the fuel supply line 114 and configured to receive inputs from the processor 122. In one embodiment, the fuel delivery system 124 is configured to control fuel flow rate into the gas turbine 116. In another embodiment, fuel delivery system 124 is configured as a fuel inhibitor unit configured to inject an inhibitor into the fuel to mitigate the effect of contaminants present. An emergency shut-off valve 126 is coupled to the fuel supply line 114 at the entry to the gas turbine 116. Optionally, a data centre 128 may be coupled to the processor 122 and configured to store various parameters of the gas turbine 116 based upon concentration levels and composition of the elements in fuel 118. In an exemplary operation of the online fuel monitoring and conditioning system 110, fuel 118 supplied to the gas turbine 116 is sampled at continuous or regular time intervals by the sampling unit 112. The elemental detection system 120 coupled to the sampling unit 112 is configured to detect multiple constituent elements and their concentrations in the fuel sample, and hence a fuel quality. The elemental detection system may include a similar configuration of crystal arrays and photon detectors as described in FIG. 1. In another exemplary embodiment, the elemental detection system 120 is configured to detect a single element such as vanadium or sodium. Fuel quality signal 123 (computed by the processor 122) may include, for example, elemental concentration in the fuel sample. In one embodiment, a command signal 123 from the processor 122 enables the inhibitor injection unit 124 to compute an inhibitor injection rate based on the concentration of the elements detected by the elemental detection system 120. Alternatively, the processor output 123 may be used to shut off the fuel supply to the gas turbine if the concentration levels of constituent elements exceed a threshold value that is dangerously corrosive or take any other corrective action thereafter. The data centre 128 is configured to continuously record the concentration of the contaminants in the fuel being fed to the gas turbine. Such aggregation of data helps in calculating various parameters, for example, maintenance cycles of the gas turbine or corrosion rate of the hot-gas path components within the gas turbine. Such parameters also help in planning preventive maintenance.

Figure 6:
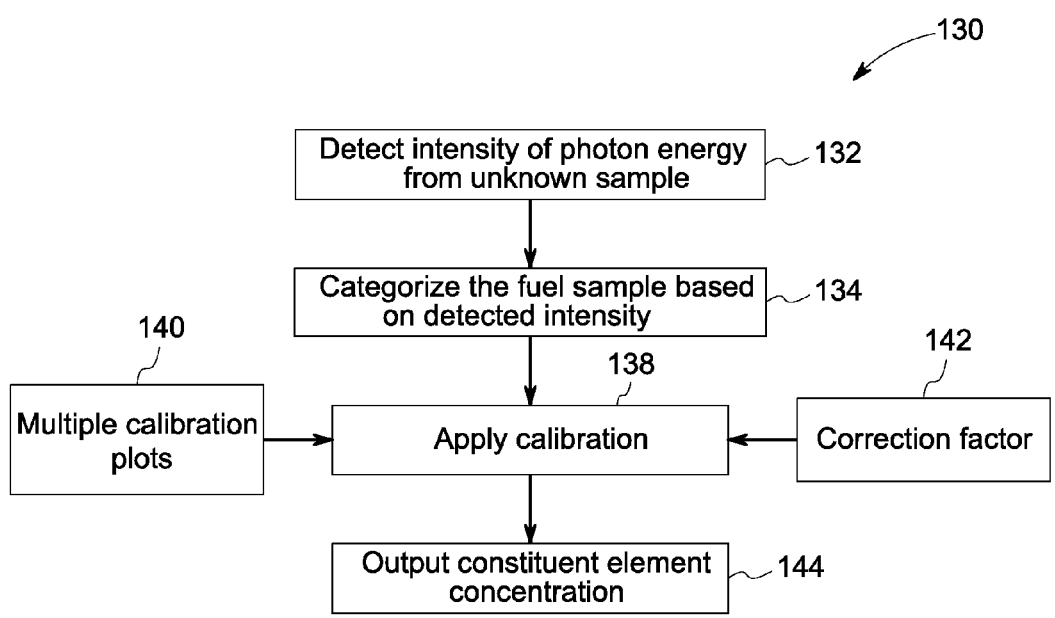
FIG. 6 is an exemplary method to detect and apply calibration based on fuel type.

Various types of liquid fuels are used in gas turbines such as crude oil, kerosene or diesel. Element detection systems as described above may detect contaminants in fuels that may be categorized from a wide range of hydrocarbon compositions. Therefore accurately detecting the X-Ray transmission signal and/or element signals in the fuel would identify a fuel type and therefore determine appropriate calibration routines to be applied based upon the fuel type. One such exemplary method to detect fuel type is illustrated in FIG. 6. The flow chart 130 illustrates various steps of identifying fuel type and accordingly applying a calibration technique according to one embodiment of the invention. The initial step 132 includes detecting fuel type by subjecting the unknown fuel sample to X-Ray radiation (as discussed above), wherein the intensity of photon energy from the sample is measured. In the next step 134, measured intensity is compared with stored intensities, for example, in the data centre, to categorize the fuel type.

A calibration is applied in step 138 wherein calibration according to one embodiment refers to the functional relationship between measured intensities from samples and the concentration of the sample. Such function is derived by measuring the photon energy intensities of a range of samples containing known amounts of the constituent elements that in turn leads to a calibration curve for a particular fuel type. Multiple such calibration curves are stored for multiple fuel types as illustrated by reference numeral 140. To determine the concentration of a constituent element in the unknown sample, the appropriate calibration determined in 134 is applied to the X-Ray signal measured in 132. The factors influencing the calibration function of the constituent element include interferences from the sample matrix and any interactions with other components in the sample. Accuracy of the concentration of the constituent elements in the unknown sample is dependent on the right calibration curve being applied. Alternatively, a correction factor (in step 142) may be applied to a stored calibration curve depending on the fuel type determined in 134 from a stored table of correction factors. The final step 144 is computation of the concentration of the element.

Advantageously, such elemental detection systems implementing array of crystals help detect low concentration levels of elements. Further, a single system may be implemented to detect multiple elements. Online systems to detect elements provide an ability to track the contaminant concentrations over time and recommend steps to initiate addition of inhibiting agents, or recommend gas turbine shutdown for inspection and cleaning prior to failure. The data logged may be used for tracking fuel contamination over time and to determine its effect on the hot corrosion in the gas turbines. Further, such online systems eliminate manual sampling, transportation to a testing facility and significant amount of time spent on sample preparation and analysis of element concentrations.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system to detect a plurality of elements, the system comprising:
   one or more X-ray sources for transmitting X-rays towards a sample;
   a plurality of photon detectors; and
   an array of crystals arranged in a curvature with appropriate geometry for receiving a plurality of photon energies emitted from the sample and focusing the photon energy on the plurality of detectors,
   wherein the plurality of photon detectors are spatially arranged at Bragg angles corresponding to signature photon energies to detect the plurality of elements simultaneously.

2. The system of claim 1, wherein the one or more X-ray sources comprises one or more high flux polychromatic beams.

3. The system of claim 1, wherein the one or more X-ray sources comprise a plurality of monochromatic beam sources.

4. The system of claim 1, wherein each crystal comprises at least one of a singly curved crystal, a doubly curved crystal or a multilayered crystal.

5. The system of claim 1, wherein each photon detector is disposed to detect an element.

6. The system of claim 1 further coupled to a fuel supply line of a power generation platform and further comprising a processor coupled to the photon detectors and configured to generate a fuel quality signal.

7. The fuel monitoring system of claim 6, wherein the processor is configured to detect concentrations of the elements and to control a supply of fuel to the power generation platform.

8. The system of claim 6, wherein the power generation platform comprises a gas turbine and the processor is further configured to compute one or more parameters of the gas turbine, wherein the parameters include maintenance schedule, hot gas path corrosion, or component corrosion based on the fuel quality signal.

9. The system of claim 6, wherein the processor is further configured to control a fuel inhibitor unit coupled to the fuel supply line.

10. The system of claim 1, wherein the sample is at least one of a solid, a liquid or a gas.

11. An online fuel monitoring system of a gas turbine comprising:
    a fuel sampling unit coupled to a fuel supply line of the gas turbine to sample a fuel in real time;
    an element detection system comprising:
    one or more X-ray sources for transmitting X-rays towards a sample;
    one or more photon detectors; and
    one or more crystals arranged in a curvature with appropriate geometry for receiving one or more photon energies emitted from the sample and focusing the one or more photon energies on the one or more detectors,
    wherein the one or more photon detectors are spatially arranged at Bragg angles corresponding to signature photon energies to detect one or more elements; and
    a processor coupled to the element detection system and configured to compute a concentration of the one or more elements in the fuel sample.

12. The online fuel monitoring system of claim 11, wherein the processor is further configured to compute a fuel quality signal.

13. The online fuel monitoring system of claim 12 further comprising a fuel inhibitor unit coupled to the fuel supply line to inject an inhibitor based upon the fuel quality signal.

14. The online fuel monitoring system of claim 12, wherein the processor is further configured to apply a calibration based on measured fuel type.

15. The online fuel monitoring system of claim 11, wherein one or more crystals are further arranged to enhance an intensity of signature photon energy.

16. The online fuel monitoring system of claim 11, wherein the elements comprise at least one of vanadium, magnesium, sodium, lithium, potassium, calcium, sulfur, nickel and lead.

17. The online fuel monitoring system of claim 11, wherein each crystal comprises at least one of a doubly curved crystal, a singly curved crystal or a multilayered crystal.

18. A system to detect vanadium in a gas turbine fuel comprising:
    one or more X-ray sources to generate and transmit X-rays towards a gas turbine fuel sample;
    two or more X-ray optic crystals arranged in a curvature to receive one or more photon energies emitted by the sample and to reflect photons having energies corresponding to vanadium; and
    a photon detector disposed at a predetermined location in a reflected path of the two or more X-ray optic crystals and configured to detect photons having an energies corresponding to vanadium.

19. The system of claim 18, further comprising a processor coupled to the detector and configured to detect a photon energy of about 4.95 kilo electron volt or wavelength of about 0.25 nanometers corresponding to vanadium in the sample.

20. The system of claim 19 wherein the processor is further configured to detect concentration of vanadium to a lower detection limit of about 0.1 ppb.

21. The system of claim 20, wherein the processor is further configured to inject inhibitor into the gas turbine fuel based upon the concentration of vanadium.

* * * * *